US012527532B2

(12) United States Patent
Knodt et al.

(10) Patent No.: US 12,527,532 B2
(45) Date of Patent: Jan. 20, 2026

(54) STRETCHER BOARD OF A PATIENT COUCH

(71) Applicant: Siemens Healthcare GmbH, Erlangen (DE)

(72) Inventors: Konstantin Knodt, Erbendorf (DE); Berthold Baumann, Kastl (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 304 days.

(21) Appl. No.: 18/325,253

(22) Filed: May 30, 2023

(65) Prior Publication Data

US 2023/0380779 A1 Nov. 30, 2023

(30) Foreign Application Priority Data

May 31, 2022 (DE) ..................... 10 2022 205 560.8

(51) Int. Cl.
*A61B 6/04* (2006.01)

(52) U.S. Cl.
CPC ................................ *A61B 6/0407* (2013.01)

(58) Field of Classification Search
CPC ........ A61B 6/0407; A61G 7/103; A61G 1/00; A61G 2210/50; A47B 13/00
USPC ..................................................... 5/601, 625
See application file for complete search history.

(56) References Cited

U.S. PATENT DOCUMENTS

| | | | | |
|---|---|---|---|---|
| 10,768,040 B2 * | 9/2020 | Taylor | .................... | A61G 7/103 |
| 2004/0060115 A1 * | 4/2004 | Panton, Jr. | ........... | A61B 6/0442 5/601 |
| 2018/0249970 A1 * | 9/2018 | Nett | ..................... | A61B 6/0407 |

FOREIGN PATENT DOCUMENTS

| | | |
|---|---|---|
| CN | 210843121 U | 6/2020 |
| JP | 2018051000 A | 4/2018 |

* cited by examiner

*Primary Examiner* — David R Hare
*Assistant Examiner* — Joseane E. Tejada
(74) *Attorney, Agent, or Firm* — Harness, Dickey & Pierce, P.L.C.

(57) ABSTRACT

One or more example embodiments relates to a stretcher board of a patient couch. The stretcher board is configured to support a patient. The stretcher board includes a hollow body with a closed monolithic lateral area, the closed monolithic lateral area including an upwardly directed sub-region defining a patient support surface, the patient support surface having an upwardly directed convex curvature.

16 Claims, 6 Drawing Sheets

STRETCHER BOARD OF A PATIENT COUCH

CROSS-REFERENCE TO RELATED APPLICATION(S)

The present application claims priority under 35 U.S.C. § 119 to German Patent Application No. 10 2022 205 560.8, filed May 31, 2022, the entire contents of which are incorporated herein by reference.

FIELD

A stretcher board of a patient couch for supporting a patient and a patient couch comprising a stretcher board are provided.

RELATED ART

Patient couches with a stretcher board are used in different fields of medical engineering. In particular, they are used to support and position a patient during medical imaging, such as, for instance, computed tomography, magnetic resonance tomography, molecular imaging or suchlike. In addition, they are also used in radiotherapeutic irradiation by means of x-ray radiation or particle radiation, in corresponding irradiation planning or in a medical intervention using imaging.

The design of stretcher boards for medical applications always takes into account a mechanical stability/rigidity of the stretcher board. This should be advantageously high in order to be able to cope with continually increasing patient weights. In addition, the design of stretcher boards for medical applications, in particular applications with x-ray radiation, e.g. the design of a stretcher board for a computed tomography (CT) system, also takes into account the imaging or x-ray absorption behavior of the stretcher board, which can have an impact on the image quality and on the x-ray dose applied to the patient. Stretcher boards for x-ray imaging are therefore ideally embodied to be x-ray transparent. High mechanical stability is typically achieved by means of increased material usage, which reduces the x-ray transparency. As a rule, the two design criteria described are therefore conflicting.

In order to achieve adequate stability of the stretcher board even with high patient weights, it is known to increase the cross-section of the stretcher board in the vertical direction. This in turn restricts a vertical traveling distance of the stretcher board in particular for adjusting movements inside a gantry of an imaging or irradiation system. Since the patient causes the stretcher board to bend as a result of his weight as soon as is positioned on the stretcher board, but a minimum distance has to be retained between the lower side of the stretcher board and the lower edge of the gantry interior, the maximum patient weight or the volume thereof is in turn restricted.

Even with stretcher boards in a "sandwich" design consisting of two layers of carbon fiber reinforced plastic (CFK) and a rigid foam intermediate layer, also known as rigid foam core, it is known to increase the area moment of inertia by means of a cross-section of the stretcher board which is designed to be higher in the vertical direction. In this way, the thickness of the CFK layers can be reduced in favor of higher x-ray transparency. However, with such stretcher boards the rigid foam core is essential in order to reduce a buckling or indentation of the upper CFK layer forming a patient support surface as a result of the patient weight. This increases the absorption of x-ray radiation through the stretcher board in addition to the CFK layers. In this way, a vertical adjustment travel for the stretcher board is also restricted.

With stretcher boards, without a rigid foam core, attempts are likewise made to achieve a high area moment of inertia and thus increased stability/rigidity in the vertical direction by means of an increased cross-section. However, this results in most cases in a deep depression in the patient support surface of the stretcher board, which in turn hampers patient transfer and reduces patient comfort.

SUMMARY

One or more example embodiments provides means for supporting or positioning a patient, which have improved mechanical stability with reduced x-ray absorption. In particular, one or more example embodiments provides means for supporting/positioning very high weight patients while simultaneously reducing x-ray absorption.

According to one or more example embodiments, a stretcher board of a patient couch and a patient couch comprise an inventive stretcher board according to the independent claims. Preferred and/or alternative advantageous embodiment variants form the subject matter of the dependent claims.

One or more example embodiments relates to a stretcher board of a patient couch. The stretcher board is embodied to support a patient. The stretcher board is embodied as a monolithic hollow body with a closed lateral area. An upwardly directed subregion of the lateral area forms a patient support surface and the patient support surface has an upwardly directed convex curvature.

BRIEF DESCRIPTION OF THE DRAWINGS

The above-described characteristics, features and advantages, as well as the manner in which these are achieved, will become clearer and more readily understandable in conjunction with the following description of the exemplary embodiments, which are explained in more detail in conjunction with the drawings. This description entails no limitation of the invention to these exemplary embodiments. In different figures, the same components are provided with identical reference characters. The drawings are in general not to scale. In the drawings.

DETAILED DESCRIPTION

Figure 1:
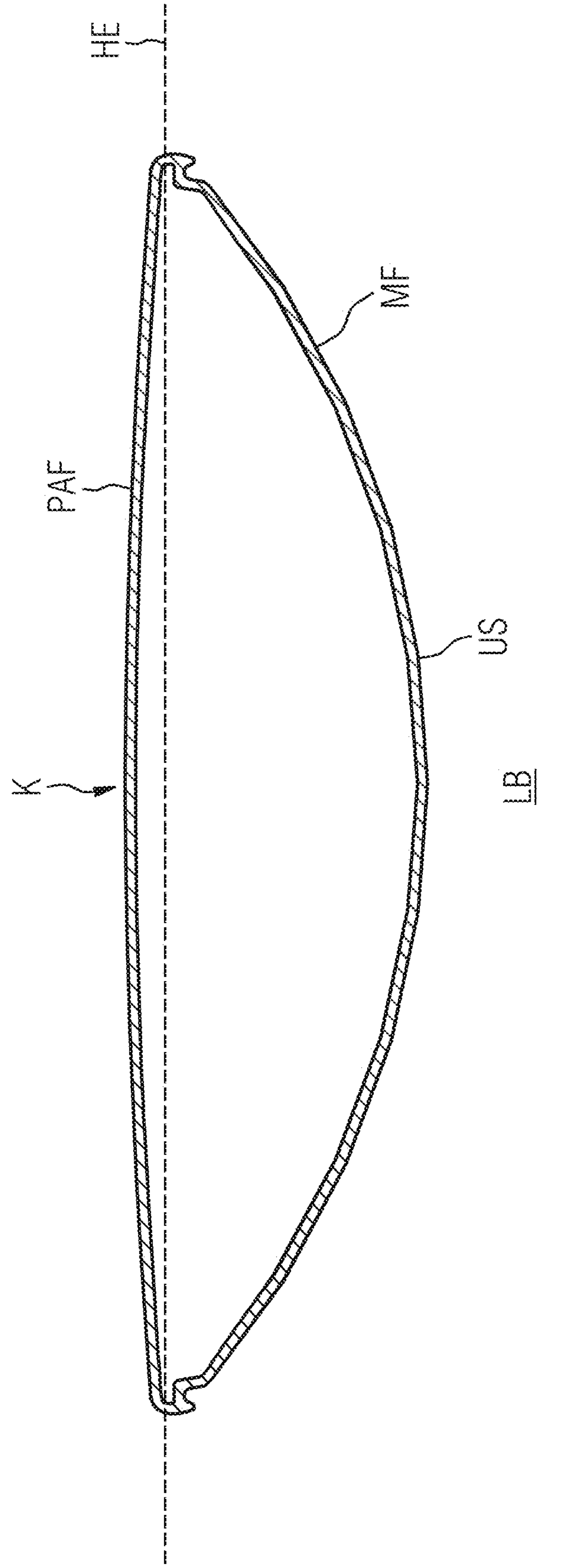
FIG. 1 shows a cross-sectional view of a stretcher board in an embodiment of the present invention.

One or more example embodiments relates to a patient couch for supporting a patient comprising a horizontal module having an inventive stretcher board.

In embodiments the patient couch is embodied as a standalone unit, said standalone unit interacting with a medical system, for instance a medical imaging system within the scope of a medical workflow. In embodiments, the patient couch is embodied as a mobile patient couch, which is designed to move in an examination or treatment environment. In a preferred embodiment, the patient couch can be embodied to move in the environment manually by means of an operator or (partially) autonomously in a motor-driven manner. In embodiments, the patient couch can comprise a corresponding bogie or at least one drive unit, for instance a motor drive.

In embodiments of the patient couch, this is embodied to adjust the stretcher board in the horizontal direction and/or in the vertical direction.

The patient couch comprises an inventive stretcher board as a component part of a horizontal module, which is also referred to as table or couch superstructure. The horizontal module of the patient couch is embodied in an embodiment of the invention to execute a horizontal or substantially horizontal adjusting movement of the stretcher board. The horizontal module is preferably embodied to execute a horizontal adjusting movement along and/or at right angles to a stretcher board longitudinal axis. Here the stretcher board can be embodied so as to be movable manually and or in a motor-driven (assisted) manner. In corresponding embodiment variants, the horizontal module comprises at least one drive unit, for instance an electric motor.

In embodiments, the patient couch is embodied to be height-adjustable. A height adjustability, in other words an adjustability along a vertical axis can be realized in embodiments by means of a vertical or lifting module. The vertical module is typically arranged between a supporting surface of the patient couch and the horizontal module. In other words, the horizontal module is arranged or fixed on an upper end of the vertical module. The adjustability in the vertical direction is preferably realized by way of a change in length of the vertical module. For instance, the vertical module comprises a scissor lift, with which the horizontal module can be adjusted to a desired height.

In further embodiments, alternatively or in addition the horizontal module can be embodied to adjust the height of the stretcher board at least over smaller distances, for instance in order to carry out a fine adjustment of the patient position in a gantry.

In further embodiments, the patient couch is embodied as a patient couch of a computed tomography system. A computed tomography system comprises a gantry, into which the stretcher board together with the patient can be introduced at least partially. In these embodiments, the horizontal module is embodied to move the stretcher board relative to a vertical module in particular in a horizontal plane and in particular along its longitudinal axis. The gantry comprises x-ray imaging components, in particular at least one x-ray radiation source and at least one x-ray detector arranged opposite thereto. X-ray radiation emitted by the x-ray radiation source is largely detected by the x-ray detector and used for three-dimensional image data generation. In order to generate measurement signals, both components rotate concentrically about the isocenter of the system in the inside of the gantry while emitting and detecting x-ray radiation. A body region of the patient to be imaged must be introduced herein by means of the inventive stretcher board.

The stretcher board is embodied to support a patient. The patient is assumed below, without restricting the generality, to mean an examination object, wherein this is in most cases a human. Essentially the patient can also be an animal. The stretcher board is therefore embodied to receive the patient per se and to support him. The patient can also be positioned by means of the stretcher board, for instance in respect of a reference coordinate system of the patient couch and/or a medical system. For this purpose, the stretcher board forms a patient support surface, on which the patient is positioned, typically reclining. The stretcher board has a length and width so that a patient can be supported entirely or substantially entirely by the stretcher board. In embodiments the stretcher board has a length in the region of 180 cm to 230 cm, preferably between 190 cm to 210 cm, particularly preferably 200 cm. In embodiments the stretcher board has a width (at right angles to the longitudinal axis) in the region of between 45 cm to 55 cm, preferably between 48 cm to 53 cm, particularly preferably 48 cm or 53 cm.

The stretcher board is embodied as a hollow body with a closed monolithic lateral area. In other words, the stretcher board or its lateral area is embodied in one piece. The lateral area of the stretcher board is preferably produced entirely with one work step. Within the context of the one or more example embodiments of the invention, a hollow body describes a body, the interior of which is hollow or empty or is only filled with air. In particular, the hollow body forming the stretcher board is not filled with a rigid foam core, as known from the prior art. The closed lateral area of the stretcher board is closed in particular in the circumferential direction in respect of the stretcher board longitudinal axis. The lateral area of the stretcher board therefore extends in a closed manner about the longitudinal axis of the stretcher board. The closed lateral area in particular extends from a stretcher board end on the face side as far as an opposing second stretcher board end on the face side in a closed manner about the stretcher board longitudinal axis.

In embodiments of the invention, the monolithic, closed lateral area of the stretcher board is embodied as a CFK component. In other embodiments, the lateral area can be formed from a material comprising aramid fibers, in particular an aramid fiber-reinforced plastic. The advantage of both alternatives is a high mechanical stability without susceptibility to corrosion and with a low net weight.

The monolithic lateral area is produced for instance by means of a suitable pressing method and a corresponding pressing core made from a blank.

As already mentioned above, an upwardly directed subregion of the lateral area forms a patient support surface, on which the patient can be supported or can be placed in a reclining manner. The patient support surface is characterised in that it has an upwardly directed convex curvature.

Within the context of one or more example embodiments of the invention, the term "upwardly" identifies a direction which points away from a supporting surface of the stretcher board and/or the patient couch or a side/area of the stretcher board which faces away from the supporting surface.

The patient support surface is therefore embodied to be curved, wherein the curvature is embodied to be convex viewed from below, in other words viewed from the direction of the supporting surface. In other words, the patient support surface of the stretcher board is embodied to be upwardly arched.

A curvature, in other words the curvature arc of the patient support surface in the stretcher board transverse axis, therefore typically runs in the direction at right angles to the stretcher board longitudinal axis. In respect of the width of the stretcher board, the highest point of the patient support surface is therefore arranged centrally. The curvature or the curvature arc typically extends across the entire width of the stretcher board.

The inventors have identified here that the formation of a curved, arched or bent patient support surface (=top side) of the stretcher board can achieve a more stable stretcher board design since the curvature advantageously prevents an at least partial buckling or indentation of the patient support surface under patient load. The wall or material thickness for the monolithic lateral area of the stretcher board with respect to known stretcher board solutions can be reduced overall by the arched formation of the patient support surface; this saves on manufacturing costs. Moreover, with thinner wall thicknesses, the applied x-ray dose also reduces for the patient or the x-ray dose required for a requisite image quality. Dispensing with the rigid form core inside the hollow body also brings about the same. The curved top side of the stretcher board moreover brings about a more hygienic design of the stretcher board, since liquids can now run off more easily. Since the patient support surface does not have depressions or is embodied under patient load, the stretcher board further advantageously simplifies a patient transfer.

Embodiments of the stretcher board, in which the wall thickness of the monolithic lateral area forming the hollow body lie in the region of between 1 mm to 1.5 mm, are preferable. In tests, adequate mechanical stability of the stretcher board could also be determined for particularly high patient weights of up to 300 kg with these wall thicknesses and the described, curved design of the patient support surface. The specified wall thickness is understood homogenously for the complete lateral area of the stretcher board.

A particularly simple manufacturing method is produced for the stretcher board when the convex curvature of the patient support surface has a curvature radius which is constant over the entire longitudinal extension of the stretcher board. In other words, the patient support surface has the same curvature or arching close to the front faces of the stretcher board and overall along the stretcher board longitudinal axis. The curvature radius is therefore identical overall. In these embodiments, the monolithic lateral area has no undercuts or edges, so that a used press core can advantageously be embodied in one piece and reusably and can be easily removed at each of the two front faces. The production costs advantageously reduce.

In alternative embodiments, in the longitudinal extension of the stretcher board the convex curvature of the patient support surface is restricted to a subregion of the patient support surface. With others the patient support surface is only partially curved. In addition, there is at least one subregion of the patient support surface, which are embodied flat or planar, in other words not curved. Here, in respect of the stretcher board longitudinal axis, the curved subregion lies behind or in front of one of the at least one subregion which is not curved. That subregion of the patient support surface in which the torso of the patient and thus the heaviest body part of the patient comes to rest is particularly preferably curved. The inventive concept therefore counteracts an unwanted load-specific bending in particular in the region of where the largest patient load has an impact.

Alternatively or in addition, in further embodiments the convex curvature of the patient support surface can have a different curvature radius in the longitudinal extension of the stretcher board. By way of example, curved subregions can pass into a non-curved subregion by means of a continual flattening out of the curvature arc or an enlargement of the curvature radius along the stretcher board longitudinal axis. Alternatively, the patient support surface can be curved convexly along the entire longitudinal extension, but with various curvature radii which change in particular continuously along the longitudinal axis. Also in these embodiments, the curvature in those subregions of the patient support surface in which the largest patient load is to be calculated is embodied most significantly. The stretcher board is embodied particularly advantageously if the curvature radii in the different subregions and the wall thickness of the closed lateral area are selected so that a flat or planar patient support surface is formed once the body weight of a patient acts on the stretcher board.

Accordingly, in particularly preferred embodiments of the invention, the curvature radius has a minimal value in a subregion of the patient support surface with the largest patient load to be expected, preferably conditioned by the torso of the patient. This subregion has the most significant curvature as a result. In embodiments, the subregion with the maximum patient load to be expected can have a length in the region of 50 cm to 90 cm, preferably 60 cm to 80 cm, particularly preferably 70 cm or 75 cm for instance.

In embodiments of the invention, the curvature radius of the convex curvature of the patient support surface assumes a value of between 1400 mm 1600 mm, preferably a value of 1450 mm. In particular, this is the (minimal) radius for a curvature or circular arc with a maximum curvature of the patient support surface. Accordingly, the patient support surface can have a larger curvature radius in further subregions and a correspondingly smaller curvature. The curvature radius is defined here in accordance with the invention as the radius of that curvature or circular arc which intersects the lateral outer edges of the patient support surface in the transverse direction of the stretcher board.

In order further to advantageously increase the area moment of inertia of the stretcher board and to counteract a load-specific deformation of the stretcher board, in further embodiments the stretcher board can further comprise at least one reinforcement element arranged on a front face or end face of the monolithic hollow body. A reinforcement element is particularly preferably attached on both front faces of the hollow body. The reinforcement element is preferably designed as a whole-surface component which supports the patient support surface against a subregion of the monolithic lateral area aligned downward, in other words in the direction of the supporting surface, on the one hand, and the lateral subregions of the lateral area running between the patient support surface and the lower subregion on the other hand. By providing the at least one reinforcement element, the wall thickness of the monolithic hollow body can advantageously be further reduced. Here the at least one reinforcement element does not contribute negatively to a reduction in the image quality, since the front faces of the stretcher board generally lie outside of the mapping region.

In embodiments, the at least one reinforcement element is manufactured from aluminum or a glass fiber-reinforced plastic.

In order to achieve a desired stability or in the case of a high patient weight required stability or a correspondingly large area of moment inertia as described above with a lower wall thickness for the stretcher board, provision is made in embodiments for the at least one reinforcement element to have a material thickness of between 30 mm and 50 mm, preferably 40 mm.

Here the required stability is therefore reached by means of an increased material usage in those regions of the stretcher board, which do not or barely influence an x-ray imaging since they are never positioned in the field of view of an imaging system. This takes place in favor of a reduced material usage in the regions of the stretcher board, which are involved in an x-ray imaging so that overall an applied x-ray dose can advantageously be kept to a minimum.

In patient couches which are part of a medical imaging system comprising a gantry or interact with such, the stretcher board is typically fixed to the same only close to one of the two front faces by means of a clamping apparatus of the horizontal module. The stretcher board itself is otherwise embodied to be self-supporting, so that it can be moved freely into and out of the gantry in a particularly simple manner by means of an adjustment unit of the horizontal module in a horizontal plane. A lowering or tipping of the self-supporting end of the stretcher board under patient load compared to the clamping point cannot be completely prevented across the length of the stretcher board of approx. 200 cm. In accordance with one or more example embodiments of the invention, provision is therefore made in embodiments for the already afore-cited subregion of the lateral area, directed downward, to have a vertical distance in respect of a central axis which runs through the stretcher board in the longitudinal extension, said central axis reducing starting from one front face toward the other front face.

Here the vertical distance reduces particularly preferably toward the self-supporting end of the stretcher board. In other words, the vertical extent of the stretcher board is embodied to be smaller at the self-supporting front face than at the front face of the stretcher board which is arranged close to the clamping point.

In this way allowance is made for the inventive stretcher board of the weight force-specific lowering of the self-supporting stretcher board end and advantageously ensures compliance of a standardized minimal distance between the stretcher board lower side and gantry interior of 25 mm even under a maximum patient load.

In this way the stretcher board forgoes increasing the vertical extent and thus enables the stretcher board to be able to be moved vertically downward also in the gantry in order to position the patient.

The vertical distance between the two front faces particularly preferably reduces by 20 mm to 30 mm, for instance by 25 mm.

FIG. 1 shows a cross-sectional view of a stretcher board LB in an embodiment of the present invention. A patient can preferably be positioned reclining on the stretcher board LB along the longitudinal axis. The stretcher board LB is embodied as a hollow body, which has a monolithic, in other words integrally formed closed lateral area MF. The hollow body is embodied to be open on its front faces or end faces. The lateral area MF has an upwardly directed subregion which points away from a supporting surface. This forms a patient support surface PAF, on which the patient is positioned or placed. The lateral area MF has moreover a subregion which points downwards, in other words in the direction of the supporting surface, which forms a lower side US of the stretcher board LB.

The patient support surface PAF has an upwardly directed convex curvature K. The patient support surface PAF is therefore not flat or planar, but instead runs in the manner of an arc between the lateral edges of the lateral area MF. The curvature K is embodied here as an upwardly directed bulge. The curvature K is currently embodied so that centrally between the lateral edges of the lateral area MF it has a maximum height difference of 2 cm in relation to a horizontal plane HE running through the lateral edges of the lateral area MF. This height difference flattens toward the lateral edges.

The hollow body has no filling and it is empty, which advantageously minimizes impairment of x-ray imaging.

As a result of the curvature K of the patient support surface PAF, the wall thickness of the monolithic lateral area MF forming the hollow body can be designed to be particularly thin without a loss of stability. The wall thickness of the lateral area MF lies here in the region of between 1 mm to 1.5 mm. The lateral area consists here of a carbon fiber-reinforced plastic and is pressed into the desired shape by applying a press core.

Figure 7:
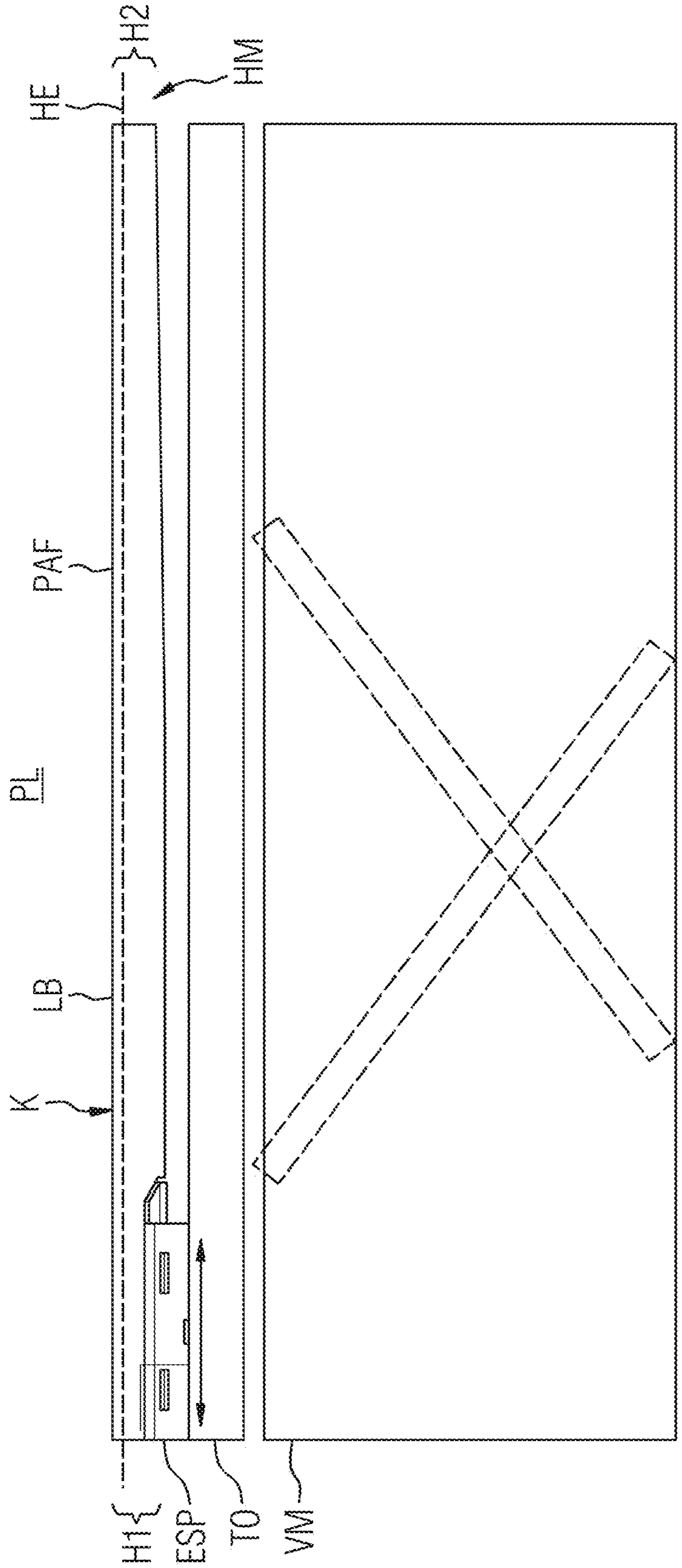
FIG. 7 shows a side view of a patient couch comprising a stretcher board in an embodiment of the invention.
Figure 8:
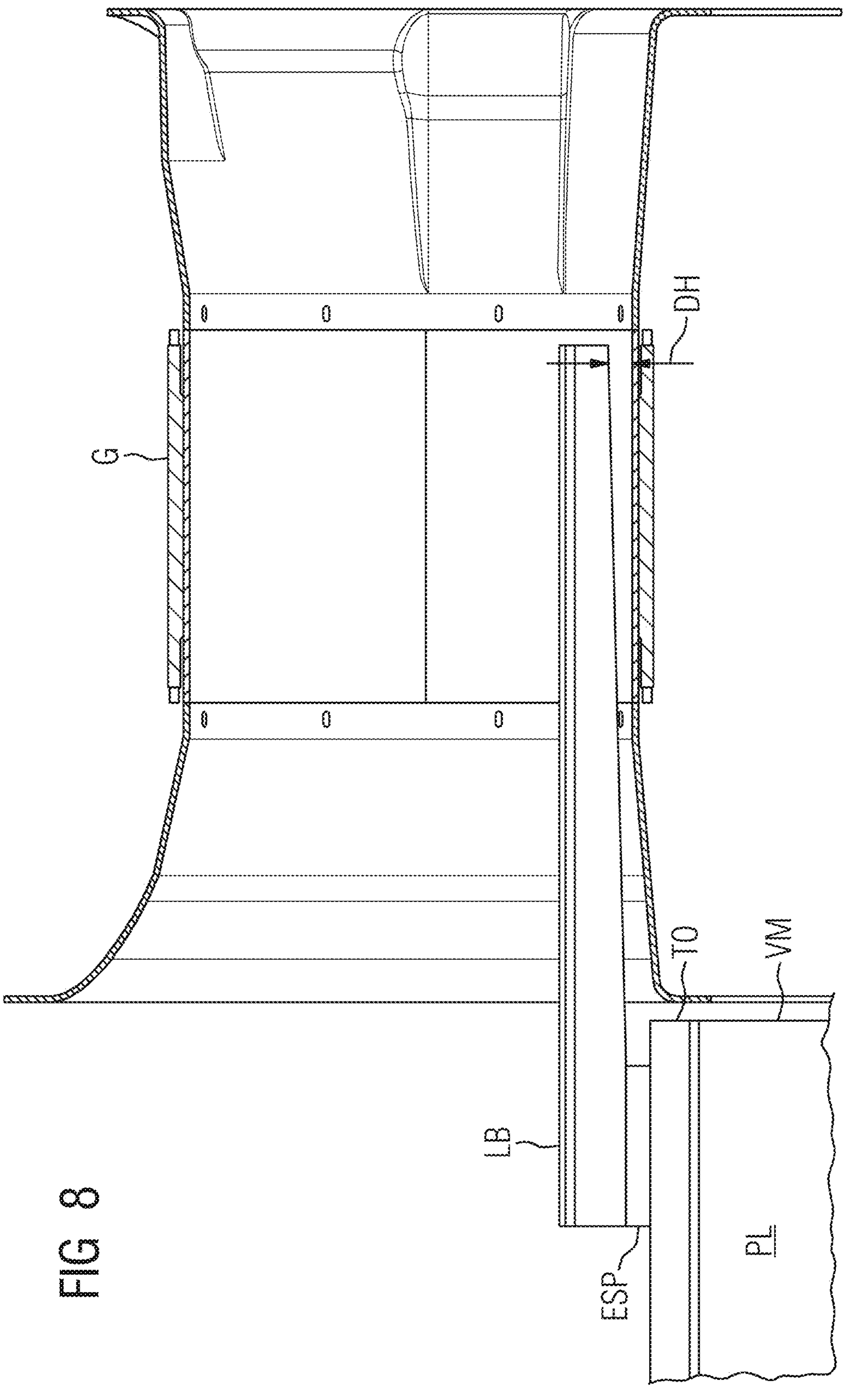
FIG. 8 shows a sectional view of a medical imaging system in the form of a computed tomography system comprising an inventive patient couch according to FIG. 7.

The stretcher board LB shown in FIG. 1, and the stretcher boards LB shown in FIGS. 7 and 8 have in each case a convex curvature K of the patient support surface PAF, which has a curvature radius which is constant across the longitudinal extension of the stretcher board. In other words, in these embodiments the curvature arc of the curvature is identical across the entire length of the stretcher board LB. The curvature K is therefore embodied in each subregion of the stretcher board LB by way of example so that centrally between the lateral edges of the lateral area MF it has a maximum height difference of 2 cm in relation to a horizontal plane HE running through the lateral edges of the lateral area MF.

In an alternative embodiment of the invention, not shown in more detail, the convex curvature K of the patient support surface PAF extends in the longitudinal extension of the stretcher board LB only across a subregion or a part of the patient support surface PAF. At least another subregion of the patient support surface is embodied to be flat or planar in this embodiment or runs in the horizontal plane HE or in parallel slightly thereabove.

In this embodiment, the lower side US of the lateral area MF is likewise embodied to be curved or arc-shaped, wherein the curvature radius of the lower side US is significantly smaller and the curvature is embodied so as to point convexly with respect to the supporting surface. The underside passes here uniformly into the lateral subregions of the lateral area MF.

Figure 2:
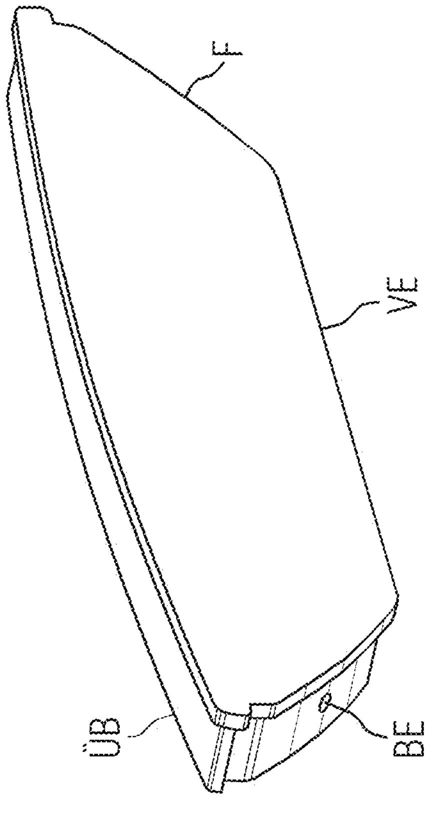
FIG. 2 shows a perspective representation of a reinforcement element according to one embodiment of an inventive stretcher board.

FIG. 2 shows a perspective representation of a reinforcement element VE according to an embodiment of an inventive stretcher board LB.

Figure 3:
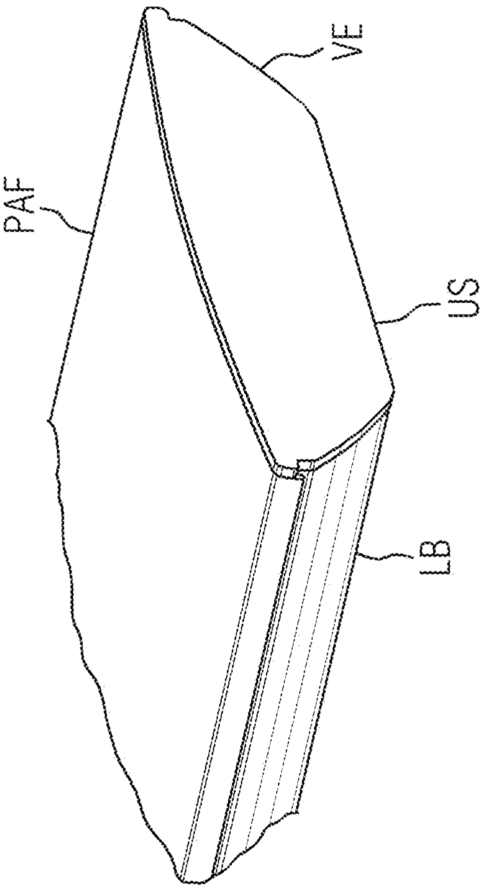
FIG. 3 shows a perspective representation of a stretcher board in an embodiment comprising a reinforcement element according to FIG. 2.

FIG. 3 shows a perspective representation of a stretcher board LB in an embodiment comprising the reinforcement element VE according to FIG. 2.

The reinforcement element VE is embodied here as a cover or cap, which can be attached to at least one and in a duplicate embodiment preferably to both front faces of the monolithic lateral area. The reinforcement element VE causes the area moment of inertia of the stretcher board LB to increase, so that the wall thickness of the lateral area can advantageously be reduced. The reinforcement element VE consists of aluminum or a glass fiber reinforced plastic. It has a front surface F, which, in the assembled state, closes the front face of the lateral area MF. In order to achieve an adequate increase in the area moment of inertia, the material thickness of the front surface F lies between 30 mm and 50 mm, here for instance 35 mm. The front surface F of the reinforcement element VE has a basic form, which corresponds in each case to a face-sided cross-section of the lateral area MF. In the embodiment of the stretcher board LB shown in FIG. 3, the underside US of the lateral area MF is embodied to be flat compared with the underside shown in FIG. 1 and runs parallel to the horizontal plane HE. The lateral subregions of the lateral area MF are here clearly distanced from the underside US and the patient support surface PAF. The reinforcement element VE comprises a tag ÜB which is inwardly offset with respect to the outer edge, and can be inserted in a form-fit manner into the lateral area MF. In addition, the tag can comprise one or more fastening elements BE, with which the reinforcement element VE can additionally be fixed to the lateral area MF. The fastening element BE can be embodied by way of example in the form of screw holes, latching hooks or suchlike, which interact with corresponding fastening elements in the lateral area in order to embody a fixed connection.

Figure 4:
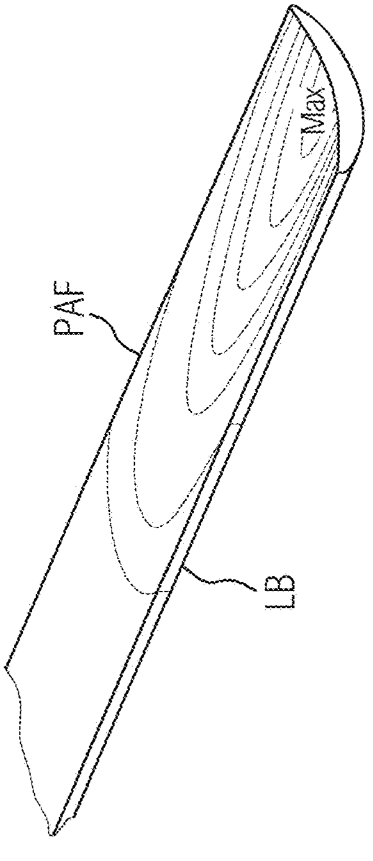
FIG. 4 shows a perspective representation of a stretcher board in an embodiment without reinforcement element under simulated patient load.

FIG. 4 shows a perspective representation of a stretcher board in an embodiment without reinforcement element under simulated patient load.

Figure 5:
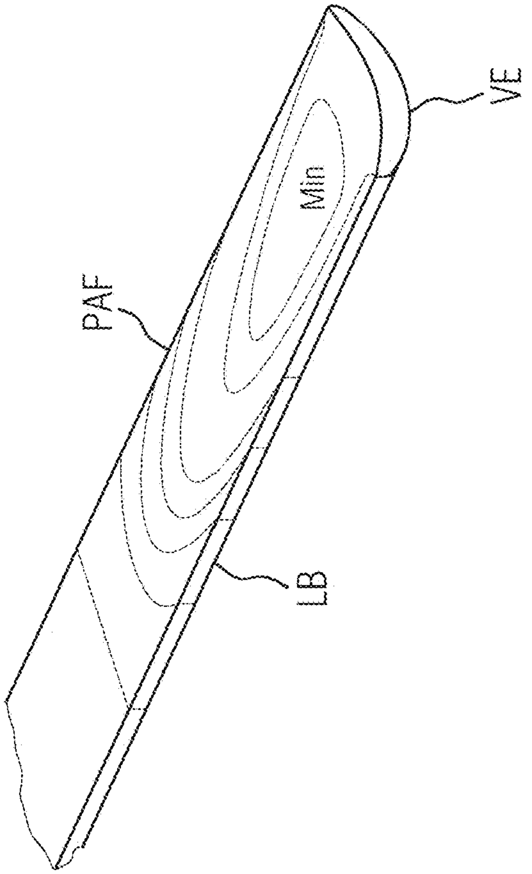
FIG. 5 shows a perspective representation of a stretcher board in an embodiment with reinforcement element according to FIG. 3 under simulated patient load.

FIG. 5 shows a perspective representation of a stretcher board in an embodiment with reinforcement element according to FIG. 3 under simulated patient load.

It can be clearly seen that the patient support surface PAF of the stretcher board LB without a reinforcement element VE is deformed or buckled significantly more as a result of the patient weight. The face-sided region of the patient support surface PAF here experiences the most significant deformation. By comparison, the formation of holes as a result of the patient weight is advantageously reduced with the reinforcement element VE.

Figure 6:
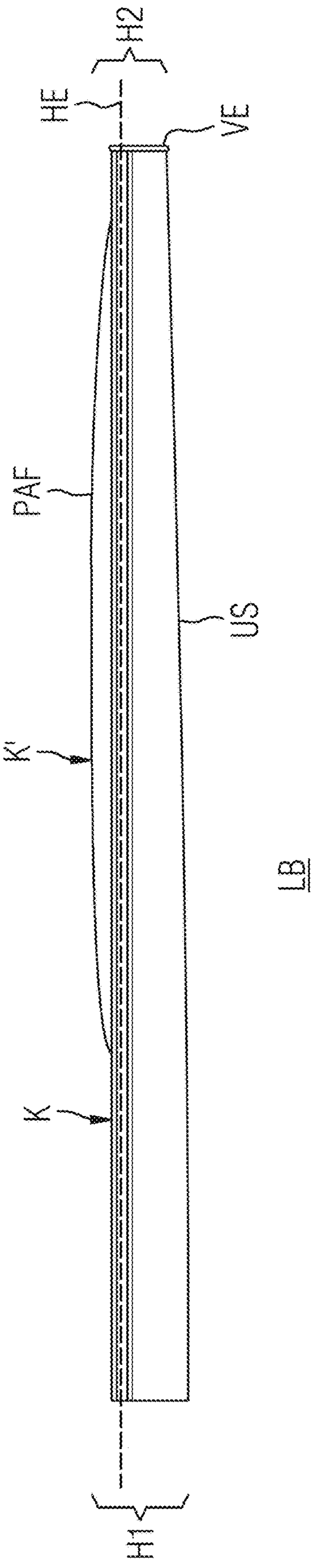
FIG. 6 shows a side view of a stretcher board in a further embodiment of the invention.

FIG. 6 shows a side view of a stretcher board in a further embodiment of the invention. Here the convex curvature K, K' of the patient support surface PAF has a different curvature radius in the longitudinal extension of the stretcher board LB. There are a number of subregions or subareas with a different degree of curvature within the patient support surface PAF. Here the curvature radius in a subarea of the patient support surface PAF is embodied smallest with the largest patient load to be expected. This subarea corresponds to the subarea with the curvature K'. In this subarea, the torso or the upper body of a patient is positioned, as expected. The curvature K' is more significant than the curvature K, there a weight force-specific deformation is counteracted more significantly than in further subareas of the patient support surface having the curvature K.

While the curvature radius for the curvature K' assumes a minimal value of 1400 mm for instance, the curvature radius for the curvature K lies at a maximum value of 1500 mm. Advantageously, within the context of patient comfort, the curvature radius passes continuously into one another across the longitudinal extension of the stretcher board LB.

The stretcher board LB shown in FIG. 6 moreover has a downwardly directed subregion of the lateral area MF, in other words a lower side US, the vertical distance of which reduces from one front face to the other front face in respect of a central axis which runs in the longitudinal extension through the stretcher board. The central axis can run here by way of example within the horizontal plane HE. In other words, the stretcher board has a first height H1 at a front face and a second height H2 at the second front face, wherein the second height H2 is lower.

The reduced vertical distance of the lower side is used for the purpose of keeping a vertical adjustment travel of the stretcher board as large as possible. As shown in FIG. 7, the stretcher board is typically fastened at one end to a table superstructure of a horizontal module HM of a patient couch PL by means of a clamping apparatus ESP. The other end of the stretcher board is embodied to be self-supporting in such an embodiment. The clamping apparatus can now be moved along the longitudinal axis of the stretcher board LB via motor or manually relative to the table superstructure. By means of this movement, the stretcher board is in particular moved in a gantry of a medical imaging system (cf. FIG. 8). Since a lowering of the self-supporting end of the stretcher board LB is to be expected when the stretcher board is loaded by the patient weight in particular, the vertical distance is particularly advantageous with respect to the self-supporting end of the stretcher board. The vertical distance between the two front faces is reduced by 25 mm for instance in order, even when the self-supporting end is lowered due to the patient weight, to comply with a standardized minimum distance between the stretcher board underside US and an inner, lower gantry edge. In embodiments with a curvature radius of the patient support surface PAF which is constant over the longitudinal axis, this corresponds to a height difference between the first and second height H1, H2 of likewise 25 mm.

FIG. 7 shows a side view of a patient couch PL comprising a stretcher board LB in one embodiment of the invention. The patient couch PL is used to support a patient and comprises a horizontal module HM having an inventive stretcher board LB. The patient couch PL also comprises a vertical module VM. The vertical module VM bears the horizontal module HM or supports this against the supporting surface. The vertical module VM is further used to adjust the height of the horizontal module HM comprising the stretcher board LB. Accordingly, the vertical module comprises a per se known lifting mechanism, which is shown here by way of example as a scissor lift mechanism. Other embodiments of the lifting mechanism are likewise conceivable. The horizontal module HM is used to adjust the stretcher board LB at least horizontally, possibly also vertically. Accordingly, the patient couch PL is embodied to adjust the stretcher board LB in the horizontal direction and/or in the vertical direction. In embodiments, the horizontal module HM can moreover be embodied to incline the stretcher board LB with respect to the horizontal plane HE. The table superstructure TO is used to connect the horizontal module HM and the vertical module VM. The table superstructure TO also comprises a clamping apparatus ESP for fixing an end of the stretcher board LB. Clamping apparatus ESP and stretcher board LB are embodied movably in relation to the table superstructure TO at least along the longitudinal axis.

The patient couch PL is preferably embodied as a patient couch of a computed tomography system G, as shown in FIG. 8.

FIG. 8 shows a sectional view of a medical imaging system in the form of a computed tomography system G comprising an inventive patient couch according to FIG. 7. The stretcher board LB of the patient couch PL is moved here into the gantry of the computed tomography system. The remaining components of the patient couch PL are located close to the gantry. Clamping apparatus ESP and stretcher board LB are moved at most in relation to the remaining stretcher components. One can clearly see the height difference DH between the lower side US of the stretcher board LB at its self-supporting end and the lower gantry inner side, which is reached by tapering the stretcher board lower side US.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where it has not yet explicitly been stated, although useful and in the spirit of the invention, individual exemplary embodiments, individual sub-aspects or features thereof can be combined and/or exchanged with one another without departing from the scope of the present invention. Advantages of the invention described in relation to an exemplary embodiment also apply, where transferrable, to other exemplary embodiments without this being explicitly stated.

The invention claimed is:

1. A stretcher board of a patient couch, the stretcher board configured to support a patient, the stretcher board comprising:

a hollow body with a closed monolithic lateral area, the closed monolithic lateral area including an upwardly directed subregion defining a patient support surface and a downwardly directed subregion, wherein the patient support surface has an upwardly directed convex curvature, a vertical distance of the downwardly directed subregion reduces with respect to a central axis running through the stretcher board in a longitudinal extension from a first front face to a second front face, and the vertical distance between the first front face and the second front face reduces by 20 mm to 30 mm.

2. The stretcher board of claim 1, wherein the upwardly directed convex curvature of the patient support surface has a curvature radius which is constant across the longitudinal extension of the stretcher board.

3. The stretcher board of claim 1, wherein the upwardly directed convex curvature of the patient support surface is restricted to a subarea of the patient support surface in the longitudinal extension of the stretcher board.

4. The stretcher board of claim 1, wherein the upwardly directed convex curvature of the patient support surface in the longitudinal extension of the stretcher board has a different curvature radius.

5. The stretcher board of claim 4, wherein a curvature radius in a subarea of the patient support surface with a largest expected patient load assumes a minimal value.

6. The stretcher board of claim 2, wherein the curvature radius of the upwardly directed convex curvature assumes a value of between 1400 mm and 1600 mm.

7. The stretcher board of claim 1, wherein a wall thickness of the closed monolithic lateral area is between 1 mm to 1.5 mm.

8. The stretcher board of claim 1, further comprising:

at least one reinforcement element on at least one of the first front face or the second front face.

9. The stretcher board of claim 8, wherein the at least one reinforcement element has a material thickness between 30 mm and 50 mm.

10. The stretcher board of claim 1, wherein the vertical distance reduces toward a self-supporting end of the stretcher board.

11. A patient couch for supporting a patient comprising:

a horizontal module, the horizontal module including the stretcher board of claim 1.

12. The patient couch of claim 11, wherein the patient couch is configured to adjust the stretcher board in at least one of a horizontal direction or a vertical direction.

13. The patient couch of claim 11, wherein the patient couch is configured for a computed tomography system.

14. The stretcher board of claim 6, wherein a wall thickness of the closed monolithic lateral area is between 1 mm to 1.5 mm.

15. The stretcher board of claim 14, further comprising:

at least one reinforcement element on at least one of the first front face or the second front face.

16. The stretcher board of claim 15, wherein the at least one reinforcement element has a material thickness between 30 mm and 50 mm.

* * * * *